United States Patent [19]

Parish et al.

[11] Patent Number: 5,506,210
[45] Date of Patent: Apr. 9, 1996

[54] PHOSPHOSUGAR-BASED ANTI-INFLAMMATORY AND/OR IMMUNOSUPPRESSIVE DRUGS

[75] Inventors: Christopher R. Parish, Campbell; William B. Cowden, Kambah; David O. Willenborg, Sterling, all of Australia

[73] Assignee: The Australian National University, Acton, Australia

[21] Appl. No.: 988,001

[22] Filed: Dec. 29, 1992

Related U.S. Application Data

[63] Continuation of Ser. No. 656,082, filed as PCT/AU89/00350, Aug. 18, 1989, abandoned.

[30] Foreign Application Priority Data

Aug. 19, 1988 [AU] Australia .................... PI9942/88

[51] Int. Cl.⁶ .................... A61K 31/70; C07H 11/04; C07H 13/00
[52] U.S. Cl. .................... 514/23; 514/825; 514/885; 536/117
[58] Field of Search .................... 514/23, 825, 885; 536/117

[56] References Cited

U.S. PATENT DOCUMENTS

| | | | |
|---|---|---|---|
| 4,096,250 | 6/1978 | Hill | 536/117 |
| 4,122,179 | 10/1978 | Vegezzi | 514/23 |
| 4,247,540 | 1/1981 | Holzmann | 424/537 |
| 4,448,771 | 5/1984 | Cattani et al. | 514/23 |
| 4,703,040 | 10/1987 | Markov | 536/117 |
| 4,739,046 | 4/1988 | DiLuzio | 536/117 |
| 4,745,185 | 5/1988 | Maryanoff et al. | 536/117 |
| 4,935,406 | 6/1990 | Coleman et al. | 514/54 |

FOREIGN PATENT DOCUMENTS

| | | |
|---|---|---|
| 596800 | 1/1987 | Australia . |
| 614772 | 4/1989 | Australia . |
| 158879 | 10/1985 | European Pat. Off. . |
| 194710 | 9/1986 | European Pat. Off. . |
| 2144332 | 3/1985 | United Kingdom . |
| 2185398 | 7/1987 | United Kingdom . |

OTHER PUBLICATIONS

Patent Abstracts of Japan, vol. 7, No. 7, issued 07 Oct. 1982, Murakami, "Production of Mannose Monophosphate salt Derivative", C144, p. 7, JP, A, 57-163491.

Patent Abstracts of Japan, vol. 12, No. 482, issued 17 Aug. 1988, Murata, "Preventive and Remedy for Hypertension", C553, p. 48, JP,A, 63-198629.

Journal of Biological Chemistry, vol. 257, No. 17, issued 10 Sep. 1982, Fischer et al., "Binding of Phosphorylated Oligosaccharides to Immobilized Phosphomannosyl Receptors", pp. 9938-9943.

Journal of Biological Chemistry, vol. 258, No. 5, issued 10 Mar. 1982, Varki et al., "The Spectrum of Anionic Oligosaccharides Released by Endo-β-N-acetylglucosainidase H from Glycoproteins" pp. 2808-2814.

Primary Examiner—Michael G. Wityshyn
Assistant Examiner—Everett White
Attorney, Agent, or Firm—Bacon & Thomas

[57] ABSTRACT

The invention relates to a method of anti-inflammatory and/or immunosuppressive treatment of an animal or human patient comprising administering to the patient an effective amount of at least one phosphosugar or derivative thereof, or a phosphosugar-containing oligosaccharide or polysaccharide or derivative thereof.

17 Claims, 1 Drawing Sheet

PHOSPHOSUGAR-BASED ANTI-INFLAMMATORY AND/OR IMMUNOSUPPRESSIVE DRUGS

This application is a continuation of U.S. application Ser. No. 07/656,082, filed Mar. 6, 1991, now abandoned, which is the U.S. national phase of International application serial number PCT/AU89/00350, filed Aug. 18, 1989.

This invention relates to phosphosugars and phosphosugar containing compounds that possess anti-inflammatory and/or immunosuppressive activity, and in particular it relates to the use of these compounds as anti-inflammatory and/or immunosuppressive agents in animals and man.

DETAILED DESCRIPTION

Figure 1:
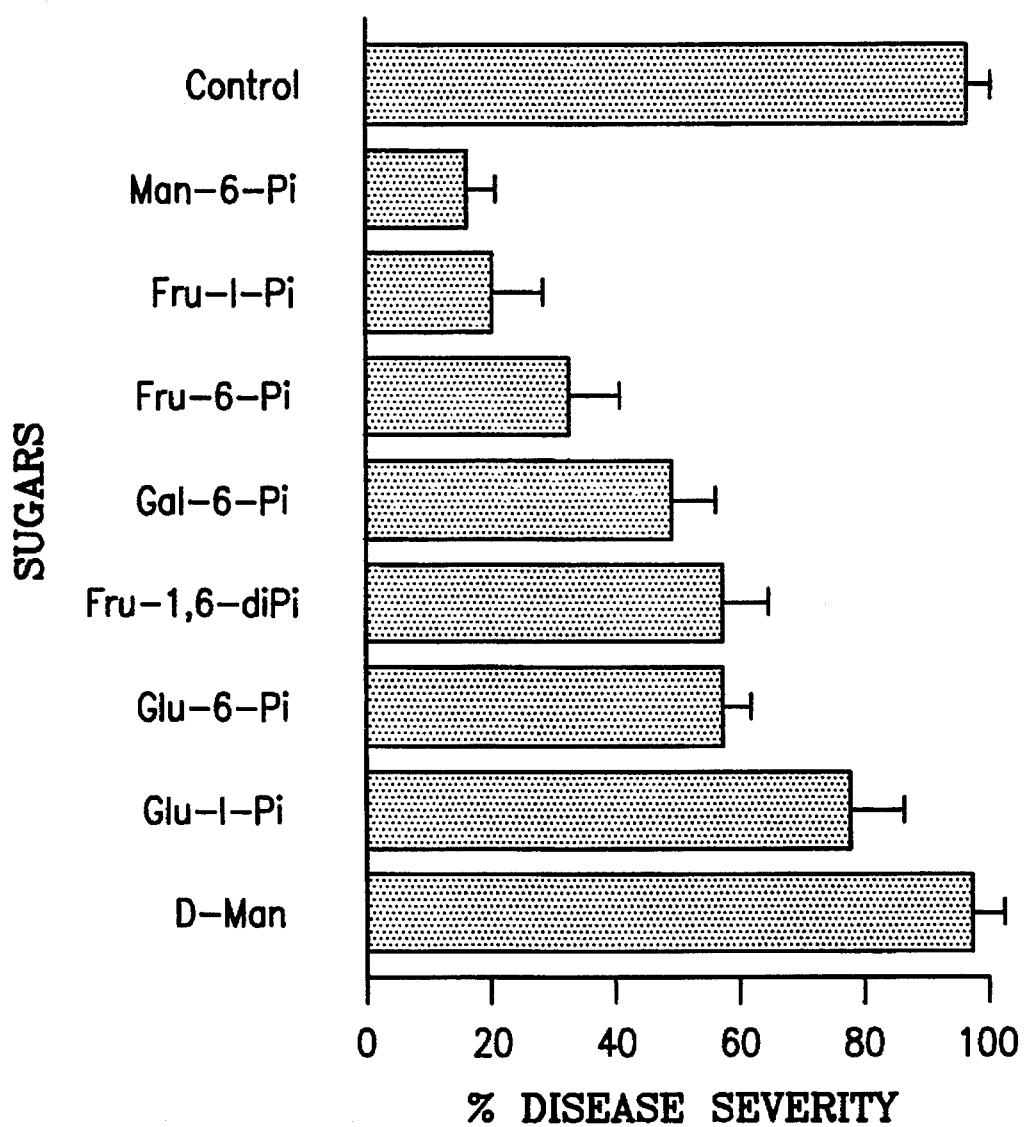
FIG. 1 is a graphical representation of the analysis of phosphosugar specificity presented in Table III.

The lysosomes of cells contain a wide range of degradative enzymes which play a central role in the entry of leukocytes into inflammatory sites. Lysosomal enzymes, produced in the rough endoplasmic reticulum, undergo glycosylation followed by a number of 'trimming' and phosphorylation reactions resulting in oligosaccharides rich in mannose-6-phosphate residues (1–3). These mannose-6-phosphate residues are specific recognition markers of lysosomal enzymes (3). It is this marker on the enzymes that is recognized by a mannose phosphate receptor (MPR) which mediates transport of lysomsomal enzymes to lysosomes. This receptor functions not only in internal transport of lysosomal enzymes but is also important in their secretory pathway and their expression on cell surfaces (1). Receptor-lysosomal enzyme interactions have been extensively studied (4–6) and shown to be inhibited by exogenous mannose-6-phosphate. Work leading to the present invention has been based on the hypothesis that mannose-6-phosphate and related phosphosugar structures might act as anti-inflammatory agents in vivo, possibly by depleting leukocytes of their lysosomal enzymes although this has not been shown previously.

As a result of these investigations, it has now been discovered that certain phosphosugars, notably mannose-6-phosphate and fructose-1-phosphate, are in fact effective anti-inflammatory agents, continuous infusion of the sugars inhibiting experimental allergic encephalomyelitis (EAE), an animal inflammatory disease of the central nervous system resembling multiple sclerosis in humans. Polysaccharides containing D-mannose with phosphate residues have also been found to inhibit EAE.

Phosphosugars, particularly mannose-6-phosphate, have also been found to exhibit an anti-inflammatory effect on passively induced adjuvant arthritis. Adjuvant-induced arthritis in the rat shares a number of features with arthritis in humans, viz. the presence of a proliferative synovitis and subcutaneous nodules, swelling of extremities, and ultimately cartilage and bone erosion. This animal model has been extensively used for detection of anti-inflammatory and immunosuppressive drugs.

Finally, phosphosugars have been found to be effective as an immunosuppressant in preliminary experiments, particularly in controlling the delayed hypersensitivity reaction.

In a first aspect, therefore, the present invention relates to the use of phosphosugars and phosphosugar-containing oligosaccharides and polysaccharides as anti-inflammatory and/or immunosuppressive agents. In this aspect, there is provided a method of anti-inflammatory and/or immunosuppressive treatment of an animal or human patient which comprises administration to the patient of an effective amount of at least one phosphosugar or a derivative thereof, or a phosphosugar-containing oligosaccharide or polysaccharide or a derivative thereof.

In another aspect, this invention relates to the use of at least one phosphosugar or phosphosugar-containing oligosaccharide or polysaccharide in the preparation or manufacture of a pharmaceutical or veterinary composition for anti-inflammatory and/or immunosuppressive treatment. In this aspect, there is provided a pharmaceutical or veterinary composition which comprises at least one phosphosugar or a derivative thereof, or a phosphosugar-containing oligosaccharide or polysaccharide or a derivative thereof, together with an acceptable pharmaceutical or veterinary carrier or diluent therefor.

Phosphosugars and phosphosugar-containing oligosaccharides or polysaccharides which may be used in accordance with the present invention comprise both naturally occurring and synthetic compounds containing or comprising phosphosugar residues, that is, sugar residues bearing at least one phosphate moiety. Particularly useful phosphosugars include phosphomannoses, phosphofructoses, phosphogalactoses and phosphoglucoses, while particularly useful oligosaccharides or polysaccharides include polysaccharides containing phosphomannose residues. Presently preferred phosphosugars include mannose-6-phosphate and fructose-1-phosphate. Preferred phosphosugar derivatives are the esters including acetate esters, particularly the 1,2,3,4-tetraacetate of mannose-6-phosphate.

Whilst it is not intended that the present invention should be restricted in any way by a theoretical explanation of the mode of action of the phosphosugars in accordance with the invention, it is presently believed that these active compounds may exert their own anti-inflammatory effect, by acting as antagonists or competitive inhibitors of the natural ligand of mannose phosphate receptors (MPR) on cells. Accordingly, the active phosphosugars or phosphosugar-containing oligosaccharides or polysaccharides may include any such compounds which are effective antagonists or competitive inhibitors of the natural ligand of the MPR.

The active anti-inflammatory and/or immunosuppressive agents in accordance with the present invention may be used to treat inflammatory diseases or conditions such as multiple sclerosis and rheumatoid arthritis, as well as in the treatment of the inflammatory process associated with the rejection of organ transplants (since massive mononuclear cell infiltrates are usually associated with acute graft rejection). These active agents may be used alone, in combination with one or more other phosphosugars, or in combination with other known anti-inflammatory or immunosuppressive agents. In particular, compositions of phosphosugars and sulphated polysaccharides with heparanase-inhibitory activity may act synergistically and represent a formulation with potent anti-inflammatory activity. The anti-inflammatory activity of these sulphated polysaccharides is disclosed in detail in International Patent Application No. PCT/AU88/00017.

The anti-inflammatory and/or immunosuppressive activity and use of the phosphosugars in accordance with the present invention is demonstrated in the following Example.

EXAMPLE 1

Inhibition of EAE.

In this Example, a number of phosphosugars and one phospho-polysaccharide were tested for their ability to inhibit development of EAE in rats. (All phosphosugars tested are commercially available and were obtained from Sigma Chemical Co., St. Louis, Mo., U.S.A.). Experimental details are included in the footnotes to the Tables setting out the test results.

Table I presents data from an EAE experiment in rats where mannose-6-phosphate, administered to animals via osmotic pumps, totally inhibited development of disease. The data presented in Table II demonstrates that a four fold reduction in the mannose-6-phosphate dose (40 mg/rat/week to 10 mg/rat/week) still resulted in a substantial reduction in disease severity, i.e. the lowest dose of phosphosugar reduced disease severity to 37.7% that of control animals.

Analysis of phosphosugar specificity revealed (Table III) that fructose-1-phosphate was as effective as mannose-6-phosphate at inhibiting disease. Fructose-6-phosphate was also a comparatively effective inhibitor of EAE, whereas galactose-6-phosphate, glucose-6-phosphate and fructose-1,6-diphosphate were partially inhibitory. Glucose-1-phosphate and D-mannose apparently had little or no effect on disease progression. These results are displayed graphically in FIG. 1. Such phosphosugar specificity closely resembles the monosaccharide specificity of the mannose-6-phosphate receptors on cells (1).

In two separate experiments (Table IV) administration of the D-mannose polysaccharide (mannan) from *Saccharomyces cerevisiae*, which contains phosphate moieties, totally inhibited EAE, indicating that phosphomannans can inhibit disease.

Histological examination of central nervous system (CNS) tissue from untreated animals with EAE and EAE animals which had been treated with either mannose-6-phosphate or mannan containing phosphate moieties, (Table V) revealed that both treatments dramatically inhibited development of CNS lesions. No lesions were detected in mannose-6-phosphate treated animals and a small number of lesions, compared with controls, in mannan treated rats. Such data are consistent with the view that the sugars are inhibiting entry of leukocytes into the CNS.

The first data column in the Tables refers to the number of animals in each group which showed any clinical signs of EAE during the entire course of the experiment. Thus, although 7/10 animals treated with mannose-6-phosphate developed some clinical signs of disease (Table III) the severity of these disease symptoms was extremely mild compared with untreated animals, i.e., <10% disease severity of controls when clinical scores and duration of disease are examined. In this sense, the mannose-6-phosphate data in Tables I and III are almost identical. Similarly, the estimation of disease severity can be used to rank the anti-inflammatory activity of phosphosugars which only partially inhibit disease, e.g., glucose-6-phosphate and fructose-1,6-diphosphate.

TABLE I

Effect of Mannose-6-Phosphate on Adoptively Transferred EAE

| Treatment | No. With EAE/Total | Mean Day Onset | Mean Clinical Score | Mean Length Disease (days) |
|---|---|---|---|---|
| Control | 8/8 | 5.2 | 3.0 | 3.5 |
| Mannose-6-phosphate | 0/8 | 0 | 0 | 0 |

Legend to Table I:
EAE induced in Lewis rats with $30 + 10^6$ ConA activated EAE effector cells. Miniosomotic pumps containing phosphosugar were implanted subcutaneously on day 3 after cell transfer. Dose was 40 mg/rat delivered over a 7 day period by 2.0 ml pumps. Clinical EAE was graded according to the following scheme: 0, asymptomatic; 1, flaccid distal half of tail; 2, entire tail flaccid; 3, ataxia, difficulty in righting; 4, hind limb weakness; and 5, hind limb paralysis.

TABLE II

Effect of Mannose-6-Phosphate Dose on Adoptively Transferred EAE

| Treatment | Dose (mg) | No. with EAE/total | Mean Day Onset | Mean Clinical Score | Mean Length Disease | Disease Severity (% Control) |
|---|---|---|---|---|---|---|
| Control | — | 4/4 | 4.5 | 3.5 | 4.5 | 100% |
| Mannose-6-Phosphate | 40 | 1/3 | 5.0 | 0.3 | 0.7 | 1.7% |
| Mannose-6-Phosphate | 20 | 4/4 | 5.0 | 1.5 | 3.0 | 28.6% |
| Mannose-6-Phosphate | 10 | 4/4 | 5.0 | 1.8 | 3.3 | 37.7% |

Legend to Table II:
Experimental details as in Table I. Mannose-6-phosphate dose represents amount of phosphosugar delivered to rats over a 7 day period via mino-osmotic pumps. "Disease Severity" represents product of mean clinical score and mean length disease.

TABLE III

Phosphosugar Specificity of EAE Inhibition

| Treatment | No. with EAE/Total | Mean Day Onset | Mean Clinical Score | Mean Length Disease (days) | Disease Severity (% Control) |
|---|---|---|---|---|---|
| Control | 9/9 | 5.0 | 3.6 | 4.2 | 100% |
| Mannose-6-phosphate | 7/10 | 6.0 | 0.9 | 1.5 | 8.9% |
| Fructose-1-phosphate | 3/5 | 5.5 | 1.2 | 1.6 | 12.6% |
| Fructose-6-phosphate | 4/5 | 6.0 | 1.6 | 2.4 | 25.4% |
| Galactose-6-phosphate | 5/5 | 5.2 | 2.0 | 3.0 | 40.5% |
| Glucose-6-phosphate | 5/5 | 5.4 | 2.0 | 3.8 | 50.3% |
| Fructose-1,6-diphosphate | 5/5 | 5.4 | 2.4 | 3.4 | 54.0% |
| Glucose-1-phosphate | 5/5 | 5.2 | 3.0 | 3.8 | 75.5% |
| D-mannose | 5/5 | 5.2 | 2.9 | 4.4 | 84.5% |

Legend to Table III:
Experimental details as in Table I. "Disease Severity" represents product of mean clinical score and mean length disease.

TABLE IV

Inhibition of Adoptively Transferred EAE by Yeast Mannan

| Treatment | No. with EAE/Total | Mean Day Onset | Mean Clinical Score | Mean Length Disease (days) |
|---|---|---|---|---|
| Expt. 1 | | | | |
| Control | 5/5 | 4.8 | 3.5 | 4.0 |
| Yeast mannan | 0/6 | 0 | 0 | 0 |
| Expt. 2 | | | | |
| Control | 4/4 | 5.0 | 3.1 | 3.7 |
| Yeast mannan | 0/4 | 0 | 0 | 0 |

Legend to Table IV:
Yeast mannan from *Saccharomyces cerevisiae* (Baker's yeast). Experimental details as in Table I.

TABLE V

Histological analysis of EAE Inhibition in Rats Receiving Mannose-6-Phosphate and Mannan

| Treatment | No. Sections scanned | No. Lesions | Lesions/section |
|---|---|---|---|
| Expt. 1 | | | |
| Control 1 | 10 | 110 | 11.0 |
| Control 2 | 8 | 206 | 25.7 |
| Mannose-6-phosphate 1 | 18 | 0 | 0 |
| Mannose-6-phosphate 2 | 15 | 0 | 0 |
| Expt. 2 | | | |
| Control 1 | 15 | 284 | 19.0 |
| Control 2 | 12 | 303 | 25.0 |
| Yeast mannan 1 | 18 | 20 | 1.1 |
| Yeast mannan 2 | 15 | 92 | 6.7 |

Legend to Table V:
Rats were killed 9 days after cell transfer and sections of the lower thoracic-upper lumbar spinal cord examined for inflammatory lesions. Animals treated as in Table I.

EXAMPLE 2

Inhibition of EAE

In further experiments using the EAE model of Example 1, other mannose phosphate-containing compounds were used, including PPME and a pentasaccharide.

PPME is the purified high molecular weight, acid-resistant fragment, (polysaccharide core fraction) of the isolated exocellular phosphomannan produced by *Pichia holstii* (*Hansenula holstii*) as described by Bretthauer et.al. (7), that contains mannose phosphate residues.

The pentasaccharide is an isolated monophosphomannopentaose fragment, 6-phospho-mannose-$\alpha$(1-3)-{mannose-$\alpha$-(1-3)}$_2$-mannose-$\alpha$-(1-2)-mannose, of the exocellular phosphomannan produced by *Pichia holstii* (*Hansenula holstii*) described by Bretthauer et.al. (7).

In these experiments, details of which were as in Table I, the number of cells transferred was $25\times10^6$/rat, while the dose of compound administered was 10 mg/rat delivered over a 7 day period by mini-osmotic pumps, commencing on day 3 after cell transfer. The results are set out in Table VI.

TABLE VI

| | Control | PPME | Pentasaccharide |
|---|---|---|---|
| EAE/Total | 5/5 | 3/5 | 1/5 |

EXAMPLE 3

Suppression of Passive Adjuvant Arthritis (DA×Lew)F1 rats were immunized with *M.butyricum* in light mineral oil given in each foot. Ten days later spleens were removed and incubated as single cell suspension tissue culture medium in +5 µg/ml ConA for 75 hrs. Cells were harvested, washed and transferred i.v. at $65\times10^6$ cells/rat into (DA×Lew)F recipients.

Treated rats were implanted on the day they received cells with miniosmotic pumps which delivered 6 mg/rat/day of mannose-6-phosphate for 14 days. Control rats were sham operated. The results are shown in Table VII as % of pre-cell injection foot size. {Average for group; n=4 (mannose-6-phosphate); n=6 (control)}.

TABLE VII

| Day | Mannose-6-Phosphate | Control |
|---|---|---|
| 4 | 97.3% | 106.4% |
| 6 | 105.8% | 129.7% |
| 7 | 102.8% | 149.7% |
| 9 | 108.4% | 148.5% |
| 11 | 107.6% | 184.2% |
| 14 | 117.4% | 220.1% |

EXAMPLE 4

Effect on Delayed-Type Hypersensitivity (DTH)

C57B1 mice were sensitised by i.v. injection $10^5$ of washed sheep red blood cells. 5 days later they were challenged in the right hind footpad with SRBC. Each mouse was given a 0.25 ml injection i/p at the same time of either saline, mannose-6-phosphate or the 1,2,3,4-tetraacetate of mannose-6-phosphate and all injections were repeated a further 6 times at approx. 3½ hour intervals. The dose in each injection of mannose-6-phosphate was 0.15 mg and of 1,2,3,4-tetraacetate of mannose-6-phosphate was also 0.15 mg. At 24 hours after challenge the DTH swelling was measured. Mannose-6-phosphate reduced the swelling by 52.5%, and the 1,2,3,4-tetraacetate of mannose-6-phosphate by 91.5%, as compared with the saline controls.

REFERENCES 1. von Figura, K. and Hasilik, A. (1986). *Ann, Rev. Biochem.* 55: 167.
2. West, C. M. (1986). *Mol. Cell. Biochem.* 72: 3.
3. Hickman, S. and Neufeld, E. F. (1972). *Biochem. Biophys. Res. Comm.* 49: 992.
4. Varki, A. and Kornfeld, S. (1983). *J.Biol. Chem.* 258: 2808.
5. Fischer, H. D., Creek, K. E. and Sly, W. S. (1982). *J. Biol. Chem.* 257: 9938.
6. Steiner, A. W. and Rome, L. H. (1982). *Arch, Biochem. Biophys.* 214: 681.
7. Brettbauer, R. K., Kaczorowski, G. J. and Weise, M. J., (1973), *Biochemistry* 12(7): 1251.

We claim:

1. A method of treatment of arthritis, of inflammatory disease of the central nervous system, to control the delayed type hypersensitivity reaction, or of the inflammatory process associated with rejection of organ transplants in a warm-blooded animal, which comprises administering to the warm-blooded animal in need thereof a therapeutically effective amount of at least one active agent selected from the group consisting of phosphomannoses, phosphofructoses and pharmaceutically acceptable salts and organic esters thereof, oligosaccharides containing phosphomannose residues, polysaccharides containing phosphomannose residues, and pharmaceutically acceptable salts and organic esters thereof, said active agent being an antagonist or competitive inhibitor of the natural ligand of a mannose phosphate receptor.

2. A method according to claim 1, wherein said active agent is selected from the group consisting of mannose-6-phosphate, fructose-1-phosphate, fructose-6-phosphate, and fructose-1,6-diphosphate.

3. A method according to claim 2, wherein said active agent is mannose-6-phosphate.

4. A method according to claim 2, wherein said active agent is fructose-1-phosphate.

5. A method according to claim 2, wherein said active agent is fructose-6-phosphate.

6. A method according to claim 1, wherein said organic ester is an acetate.

7. A method according to claim 6, wherein said organic ester is the 1,2,3,4-tetraacetate of mannose-6-phosphate.

8. A method according to claim 1, wherein said oligosaccharide or polysaccharide is the D-mannose polysaccharide (mannan) from *Saccharomyces cerevisiae*.

9. A method according to claim 1, wherein said oligosaccharide or polysaccharide is the purified high molecular weight, acid-resistant fragment (polysaccharide core fraction) of the exocellular phosphomannan produced by *Pichia holstii* (*Hansenula holstii*), or an oligosaccharide fragment derived therefrom.

10. A method according to claim 9, wherein said oligosaccharide fragment is the monophosphomannopentaose fragment, 6-phospho-mannose-α(1-3)-{mannose-α(1-3)}$_2$-mannose-α-(1-2)-mannose.

11. A method according to claim 1, wherein said treatment comprises treatment of inflammatory disease of the central nervous system.

12. A method according to claim 1, wherein said treatment comprises treatment of arthritis.

13. A method according to claim 1, wherein said treatment comprises treatment to control the delayed-type hypersensitivity reaction.

14. A method according to claim 1, wherein said treatment comprises treatment of rheumatoid arthritis.

15. A method according to claim 1, wherein the treatment is of the inflammatory process associated with the rejection of organ transplants.

16. A method of treating arthritis in an animal subject, which comprises administering to the subject a therapeutically effective amount of mannose-6-phosphate or a pharmaceutically acceptable salt or organic ester thereof.

17. A method of treating inflammatory disease of the central nervous system in an animal subject, which comprises administering to the subject a therapeutically effective amount of mannose-6-phosphate, fructose-1-phosphate, or a pharmaceutically acceptable salt or organic ester thereof.

* * * * *